United States Patent [19]

Burns et al.

[11] 4,124,908
[45] Nov. 14, 1978

[54] RESCUE AND TRANSPORTATION DEVICE

[76] Inventors: Oliver E. Burns, 11113 Sudith Ave., Fountain Valley, Calif. 92708; Robert C. Day, 2089 Balmer Dr., Los Angeles, Calif. 90039

[21] Appl. No.: 839,797

[22] Filed: Oct. 6, 1977

[51] Int. Cl.² .......................... A61F 13/06; A61F 5/04
[52] U.S. Cl. ........................................ 5/82 R; 2/69.5
[58] Field of Search .................. 5/82 R, 121; 2/69.5

[56] References Cited

U.S. PATENT DOCUMENTS

| | | | |
|---|---|---|---|
| 2,410,181 | 10/1946 | Peters | 5/82 |
| 2,489,829 | 11/1949 | Springer | 5/82 |
| 2,899,692 | 8/1959 | Finken | 5/82 |
| 3,158,875 | 12/1964 | Fletcher | 5/82 |

*Primary Examiner*—Casmir A. Nunberg

*Attorney, Agent, or Firm*—John G. Mesaros

[57] ABSTRACT

A rescue and transportation device constructed of flexible cloth-like material and including a bottom portion for receiving a victim, the bottom portion having a head end and a foot end with longitudinally extending first and second side flaps, the foot end and side flaps being configured for substantially surrounding the body. The foot end includes reinforcing members and the head end includes a head restraining device. Reinforcing webbing encircles the body lengthwise with spaced lateral webbing providing support adjacent the jointed portions of the body, the webbing when fastened, in conjunction with the head restraining device and foot supporting end, substantially immobilizing the body to create body rigidity utilizing the body's own weight and physical characteristics for transporting the victim.

10 Claims, 7 Drawing Figures

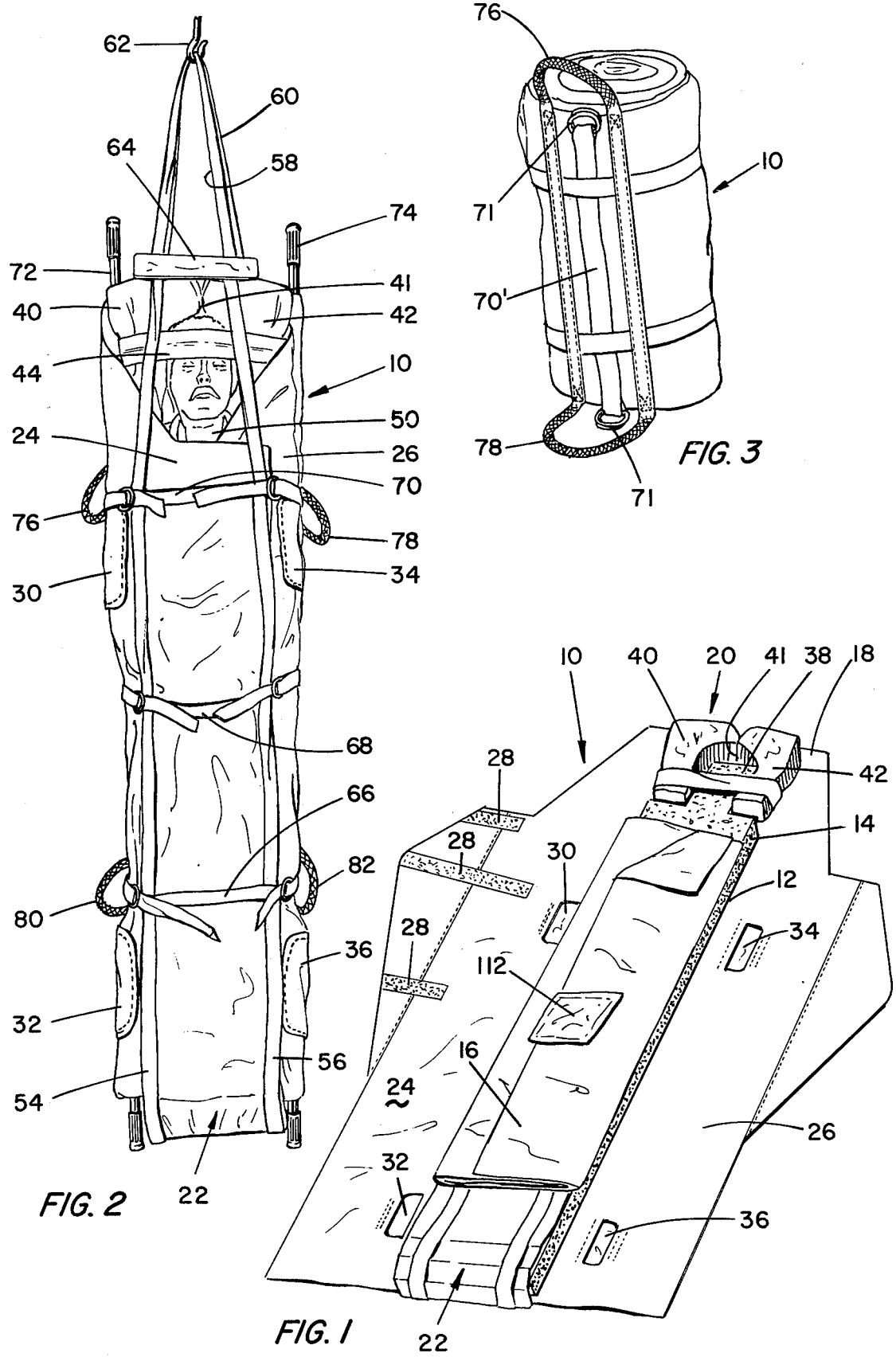

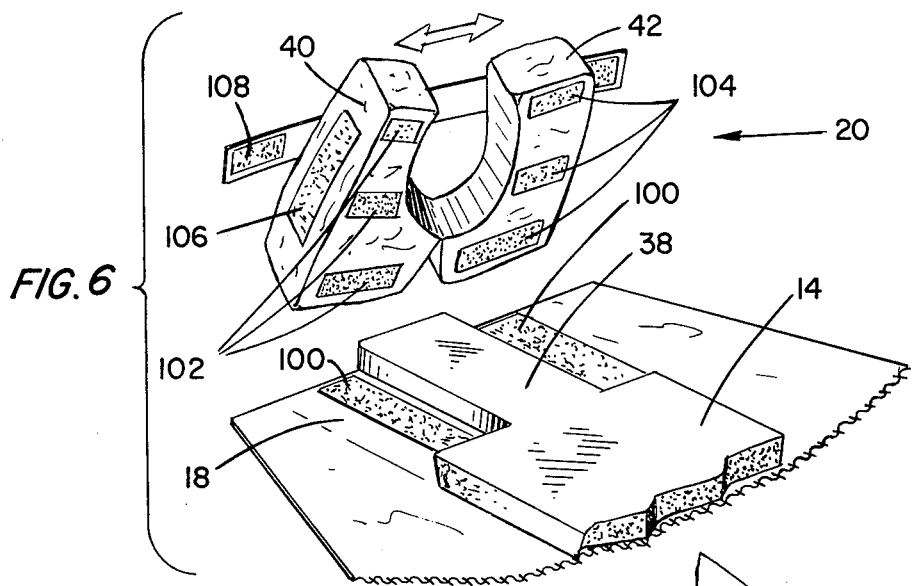
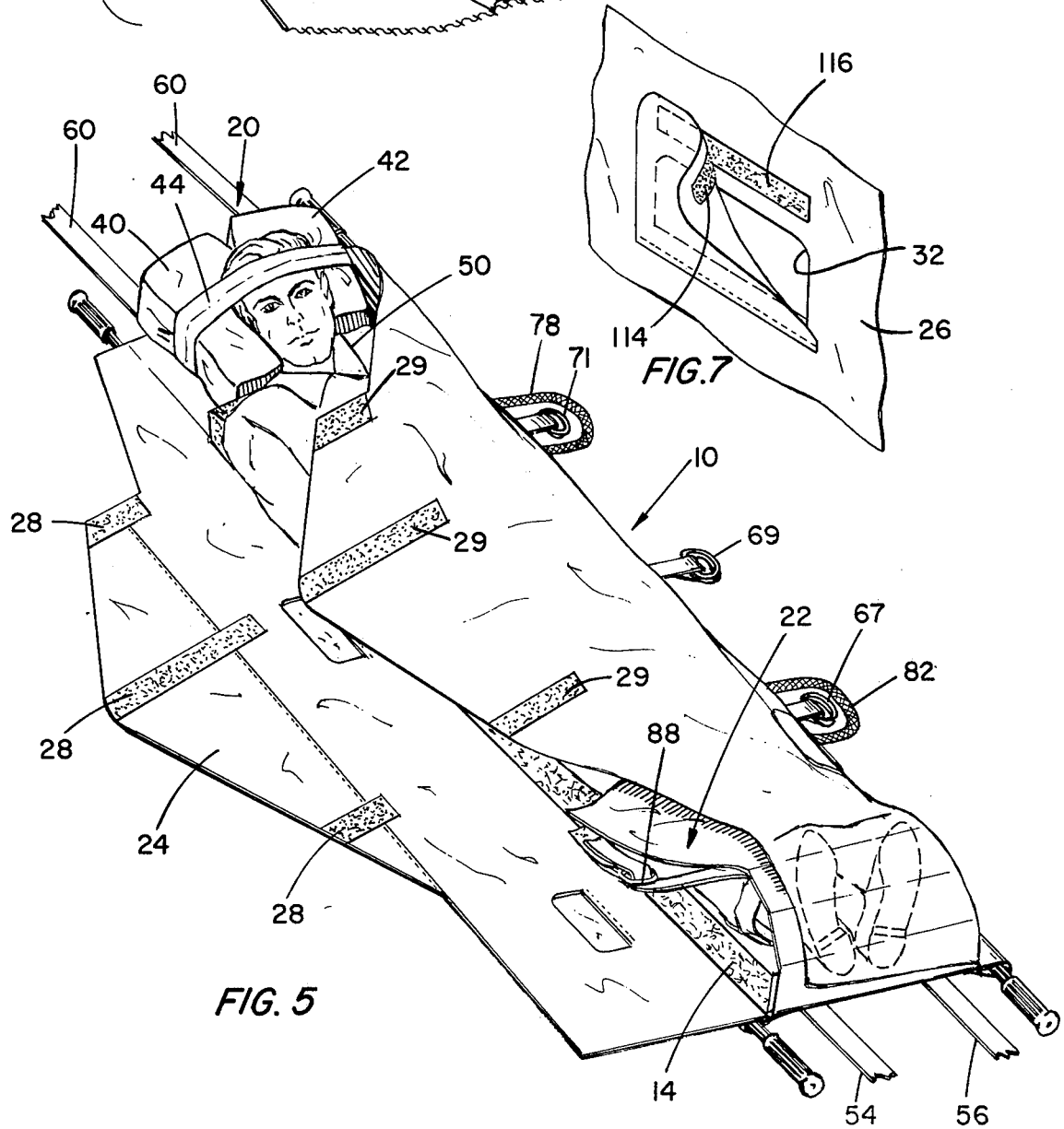

RESCUE AND TRANSPORTATION DEVICE

BACKGROUND OF THE INVENTION

The background of the invention will be discussed in two parts:

1. Field of the Invention

This invention relates to rescue and transportation units and more particularly to such a unit formed of flexible cloth-like material which may be bundled into a compact size for storage.

2. Description of the Prior Art

In emergency evacuation or rescue situations, difficulty is oftentimes encountered due to the location of the victim and the lack of knowledge as to the extent of injuries of the victim. Many times access to the victim for the purpose of administering first aid and removing the victim from confined areas such as mines or caves, below ships decks, in mountainous terrain or isolated areas requires intricate and arduous maneuvering of the victim which may complicate the injuries suffered by the victim. In most of such instances, it is desirable, where possible, to substantially immobilize the victim to the maximum extent possible to prevent complications. One such device for transporting victims is in the form of a substantially rigid basket into which the victim is placed and strapped. However, the utility of such a basket is limited where the opening through which the basket must pass is smaller than the overall cross section of the basket, thereby substantially limiting its utility. Furthermore, such baskets when utilized for mass evacuation by helicopter present a space problem inasmuch as the number of such baskets which can be transported at one time are determined by the amount of space available within the helicopter, and correspondingly when ground vehicles are utilized, the same problem would exist.

In civil disaster situations, such as automobile accidents or the like, conventional cot-type stretchers may be employed, such stretchers generally being employed in conjunction with other blankets and the like where the victims are suffering from trauma/ shock or burns. However, such conventional stretcher units are not readily equipped for restraining the head of the victim, movement of which during transportation could conceivably compound injuries already suffered.

An emergency burn treatment pack is shown and described in U.S. Pat. No. 3,986,505 issued to Ronald A. Power on Oct. 19, 1976, including a flexible waterproof outer covering having a pair of interlocking portions with a sterile sheet placed over a resilient foam material with the sheet and the foam being saturated with an aqueous solution prior to placing the burn patient thereon. The outer covering then substantially surrounds the patient in a sterile moist atmosphere. The outer covering is provided with lengthwise loops for accepting poles for carrying the patient. Such a device, however, is not readily usable for evacuation in the difficulty of access situations hereinabove referred to.

Accordingly, it is an object of this invention to provide a new and improved rescue and transportation device.

It is a further object of this invention to provide a new and improved rescue and transportation device for use in inaccessible areas.

It is an additional object of this invention to provide a new and improved rescue and transportation device which substantially immobilizes the body of the victim.

It is still another object of this invention to provide a new and improved rescue and transportation device which provides protection of the victim's body against trauma/shock and burns.

It is a still further object of this invention to provide a new and improved rescue and transportation device which substantially immobilizes the body to create body rigidity for utilizing the body's own weight and physical characteristics for transporting the victim.

SUMMARY OF THE INVENTION

The foregoing and other objects of the invention are accomplished by providing an outer covering of a flexible cloth-like material, the covering including a bottom portion for receiving the victim, the bottom portion having a head end and a foot end with longitudinally extending first and second overlapping side flaps, the foot end and side flaps being configured for substantially surrouding the body. Pockets are provided in the foot end and the head end for receiving reinforcing members. A head restraining device is releasably coupled to the head end for providing lateral support for immobilizing the head. Web means are secured to the bottom portion, the web means encircling the body lengthwise with spaced lateral webbing providing lateral support adjacent the jointed portions of the body, the webbing, when fastened, in conjunction with the head restraining device and foot supporting end, substantially immobilizing the body to create body rigidity for utilizing the body's own weight and physical characteristics for transporting the victim. The webbing when so fastened, also provides means adjacent the head end for lifting the body in a vertical attitude. Auxiliary disposable accessory articles are provided for burn or shock/trauma treatment. The side flaps are further provided with access openings for life sign detection or drug administration.

Other objects, features and advantageous of the invention will become apparent from a reading of the specification when taken in conjunction with the drawings in which like reference numerals refer to like elements in the several views.

BRIEF DESCRIPTION OF THE DRAWINGS

FIG. 1 is a perspective view of the rescue and transportation device according to the invention;

FIG. 2 is a front view of the rescue and transportation device in its operative position suspending a victim therein in a vertical attitude;

FIG. 3 is a perspective view of the rescue and transportation device in a stored position;

FIG. 5 illustrates a victim partially contained within the rescue and transportation device of FIG. 1;

FIG. 6 is an exploded perspective view of the head end of the rescue and transportation device with the head restraining device in disassembled relation therewith; and FIG. 7 is a partial perspective view of an access opening in the side flap of the rescue and transportation device of FIG. 1.

DESCRIPTION OF THE PREFERRED EMBODIMENT

Figure 4:
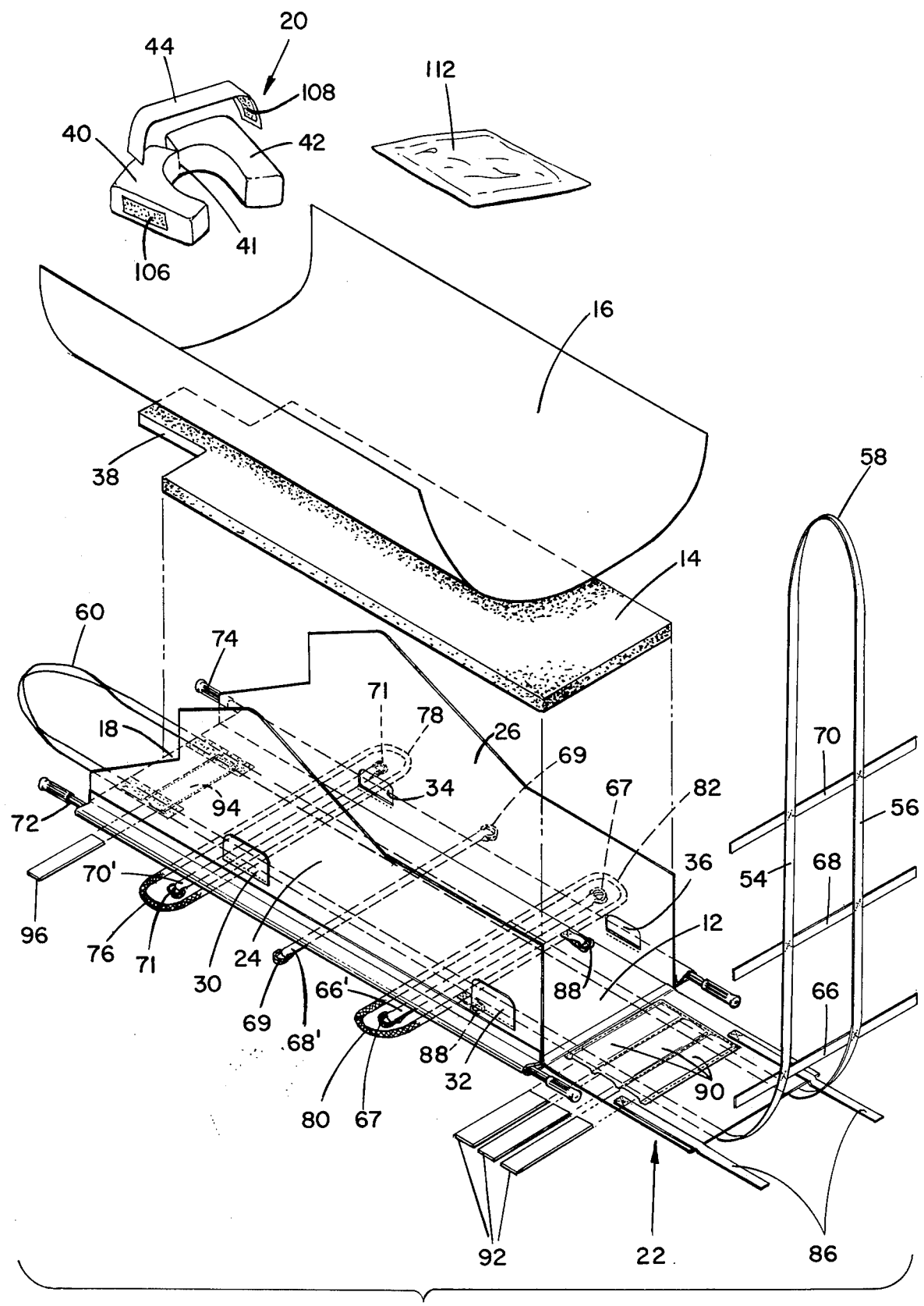
FIG. 4 is an exploded perspective view of the rescue and transportation device of FIG. 1.

Referring now to the drawings and particularly to FIG. 1, there is shown a rescue and transportation device generally designated 10 including a flexible outer covering having a centrally disposed longitudinally extending bottom portion 12 having resting thereon a foam pad 14 with a liquid impervious sheet member 16 resting thereon and adapted for receiving the body of the victim and covering the same. The bottom portion 12 has a head end generally designated 18 which includes a head restraining device generally designated 20, the bottom portiin 12 also having a foot end generally designated 22. Extending outwardly from opposite longitudinal edges of bottom portion 12 are first and second overlapping side flaps 24 and 26, respectively, the two flaps being configured for substantially surrounding the body of the victim when placed on sheet 16 with side flaps 24 and 26 in overlapping relationship. The interior of side flap 24 is provided with a plurality of Velcro strips 28 with the outer surface of side flap 26 being provided with mating strips (not shown) in aligned relationship with the Velcro strips 28 for securing the side flaps 24 and 26 in overlapping relationship.

The side flap 24 is provided with first and second access openings 30 and 32, the access openings 30 and 32 being so-positioned to provide access to the right arm and right leg of a victim placed within the rescue and transportation device 10. Correspondingly, side flap 26 is provided with first and second access openings 34 and 36 for access to the opposite members of the victim.

As shown in FIGS. 1 and 4, the foam pad 14 is generally rectangularly configured with a projecting portion 38 adjacent the head end thereof, the portion 38 being configured to receive the head of the victim. The lead restraining device 20 includes first and second contoured cushioned members 40 and 42 fitted within a common covering to provide a hinge 41 at the connecting point thereof, the so-connected cushion members forming a generally U-shaped device with the opening thereof configured for receiving the head therein to provide lateral support. As can be seen in FIG. 1, the cushion members 40 and 42, in the operative position abut against opposite edges of the projecting portion 38 of the foam pad 14. A releasable strap member 44 may be secured laterally across the opening of the head restraining device 20 at various locations as will hereinafter be described for restraining the head of the victim to prevent movement away from the projection portion 38 of foam pad 14.

Referring now to FIG. 2, the rescue and transportation device 10 is illustrated with a victim 50 positioned therein, the device 10 being supported in a vertical attitude for lifting in a vertical direction such as the lifting that might be utilized for transporting the victim to a helicopter or the like. The head of the victim 50 has the releasable strap member 44 of the head restraining device 20 laterally positioned across the forehead with the head fitting within the opening intermediate cushion members 40 and 42 for restraining the head from lateral and forward movement. With the flaps 24 and 26 in secured overlapping relation about the body of the victim 50 and the foot end 22 encircling the feet with suitable reinforcing members therein as will hereinafter be discussed, the body of the victim 50 is secured by suitable web means. The bottom of the bottom portion 12 of the rescue and transportation device 10 has secured thereto, such as by sewing, portions of first and second spaced web members 54 and 56 which encircle the body lengthwise with the ends thereof forming loops 58 and 60, the loops 58 and 60 being adapted for gripping by a hook device 62 for vertically lifting the victim 50 within the device 10. The vertical or longitudinally extending straps 54 and 56 are generally parallel and a spreader bar 64 is releasably and slidably connected to the web means 54 and 56 adjacent the loop ends 58 and 60 thereof above the head of the victim 50, the spreader bar 64 serving two purposes, one being to keep the webs 54 and 56 away from the head and face of the victim 50, and the second purpose being to prevent the device 10 from turning during the vertical lifting of the device 10 with the victim 50 mounted therein.

The device 10 is further provided with spaced lateral webbing means such as webs 66, 68 and 70, each of the lateral web means being positioned adjacent a flexing portion of the body to provide lateral support. For example, the web 66 encircles the body of the victim 50 adjacent the knees while web 68 encircles the body of the victim 50 adjacent the hips or waist thereof with web 70 encircling the body of victim 50 below the shoulders thereof adjacent the chest portion. The locations of lateral web members 66, 68 and 70 or selected to limit the flexing of the normally flexed portions of the body to thereby utilize the body's own weight and physical characteristics to provide a measure of rigidity of the rescue and transportation device 10 with the victim 50 therein to provide a compact stretcher-type device having outside dimensions generally no greater than the body of the victim. As will hereinafter be discussed, lateral reinforcing members are positioned with pockets in the centralmost bottom portion 12 of the device 10 for providing rigidity adjacent the head of the victim 50 as well as at the foot end 22 to protect the victim 50 while permitting evacuation of the victim, for example, in air to sea, air to ground, or ship to ship rescue situations, or to transport the victim from confined and isolated areas where ordinary stretcher equipment is too large, bulky, and burdonsome for effective use. The device 10 may also include optional break away poles 72 and 74 which extend through slots formed longitudinally on opposite sides of the exterior of bottom portion 12 of the device 10.

As shown in FIG. 3, with the poles 72 and 74 broken down into smaller sections, the device 10 may be conveniently folded for storage into a compact size of approximately 26 inches long by approximately 10 inches in diameter and can be carried by means of flexible straps 76 and 78 sewed to the outer surface thereof in a continuous loop to provide additional lateral support on opposite sides of one portion of the web 70. The handles 76 and 78, as shown in FIG. 2, along with a second pair of handles 80 and 82 provide means along opposite longitudinal edges of the device 10 for carrying the victim 50 when the poles 72 and 74 are not utilized. The handles 76 and 78 are positioned on opposite sides adjacent the chest area of the victim 50 while the handles 80 and 82 are positioned opposite sides of the knee area of the victim 50 adjacent lateral web 66. These carrying points are likewise selected so that with the victim 50 positioned therein, without the poles 72 and 74 the device 10 envelopes the body of the victim 50 in such a way that minimum flexing of the body results from carrying the victim by means of the two pairs of strap members 76, 78, 80 and 82.

Referring now to FIG. 4 the device 10 is shown in exploded perspective illustration with the webbing and strap means illustrated in dotted lines to show the locations and dimensions thereof relative to the overall unit. The bottom portion 12 of the flexible outer covering is generally rectangular in form with the foot end 22 being a flap having secured to the undersurface thereof a pair of parallel spaced straps 86 having a length longer than the length of the flap, the free ends of straps 86 being adapted for securing to D-rings 88 secured to the upper surface of the bottom portion 12 in proximate location to the lateral support web 66. The flap of foot end 22 is provided with a plurality of pockets 90 which extend laterally for receiving therein suitable reinforcing members 92 which are slats which may be formed of aluminum, plastic, wood or any other structurally generally rigid material. On the undersurface of bottom portion 12 adjacent the head end 18 thereof, a laterally extending pocket 94 is formed for receiving therein a similar reinforcing member or slat 96, this location being adjacent the neck of the victim 50.

The longitudinally extending web means for encircling the body lengthwise is basically a continuous loop web having an overall looped length in excess of twice the maximum length or height of the victim with sufficient length to form the loops 58 and 60 previously discussed. A first portion on the longitudinal webs 54 and 56 is secured to the undersurface of the bottom portion 12 of the outer covering such as by sewing or the like, with the greater part of the continuous loop being configured for positioning over the front of the victim after the side flaps 24 and 26 are suitably secured. Each of the lateral web means 66, 68 and 70 is configured for encircling the body laterally at preselected locations and may take any convenient form. In the illustrations shown, the lateral web means consists of first web 66, 68 and 70 with a second set of webs with which each coacts and fastens being designated by the same numeral with a "prime" thereafter, the second webs being designated 66', 68' and 70', each of the later mentioned webs being secured laterally on the undersurface of bottom portion 12 with the free ends thereof having secured thereto D-rings 67, 69 and 71, respectively. The webs 66', 68' and 70' are secured by sewing, for example. Each of the webs 66, 68 and 70 is sewn to the longitudinally extending webs 54 and 56 with free ends on either side of the longitudinal webs 54 and 56, these free ends being configured for frictionally engaging the D-rings 67, 69 and 71, respectively, for securing the victim within the device 10.

Referring to FIGS. 1, 4 and 6, the head restraining device will be discussed in detail. As previously mentioned, the head restraining device 20 has the contoured cushions 40 and 42 thereof configured for positioning alongside projecting portion 38 of the foam pad 14, and as best illustrated in FIG. 6, the head end 18 of the bottom portion 12 of the outer covering is provided with Velcro strips 100 positioned lengthwise on either side of the projecting portion 38 of the foam pad 14. The undersurface of the covering of each of the contoured cushion members 40 and 42 is provided with laterally extending Velcro fastening strips 102 and 104, respectively, for enabling the undersurface of the cushion members to be suitably secured to the bottom portion 12 of the device 10. In this manner, the head restraining device 20 can be adjusted longitudinally with resepect to the head of the victim and correspondingly the free ends of the legs of cushion members 40 and 42 may be adjusted laterally to provide lateral support for the head of the victim 50. Similarly, on opposite outer surfaces of the covering of cushion members 40 and 42, other Velcro strips 106 (only one of which is shown) are sewn for engagement by mating Velcro strips 108 on the undersurface of other end of the head restraining strap member 44, the fastening strips being so-positioned and so-configured to permit adjustment of the effective length of the strap member 44 in the lateral direction as well as permitting flexibility in the placement thereof in the longitudinal direction along the length of Velcro strip 106. Generally, the head restraining strap 44 would be positioned over the forehead of the victim.

Referring now to FIG. 5, a victim 50 is shown in position with the rescue and transportation device 10 partially encircling the body of the victim 50. With the foam pad 14 positioned on the bottom portion 12 of the device 10 and the liquid impervious sheet or liner 16 placed thereon, the victim 50 is then placed on the sheet 16 which is then folded over to the front part of the body of the victim 50. The foot end 22, with the slats 92 within pockets 90 thereof (see also FIG. 4) is then folded over the feet of the victim and the straps 86 thereof are secured to the D-rings 88 which are secured to the bottom portion 12. In this manner, the foot end flap 22 provides rigid support for supporting the feet of the victim, even in a vertical position, if necessary.

The head restraining device 20 is then positioned about the head of the victim 50 with the contoured resilient cushion members 40 and 42 in abutting relation with the side of the head, the cushions 40 and 42 then being depressed downwardly to permit fastening of the respective Velcro strips on the undersurface of the head restraining cushion members 40 and 42 in the adjacent surface of the head end 18 of the bottom portion 12 of the device 10. With the cushions 40 and 42 thus "locked" in position, lateral support is provided for the head. The strap member 44 is then positioned across the forehead of the victim 50 with the ends of strap member 44 being depressed downwardly and inwardly to permit the Velcro strips 108 thereof to engage the Velcro strips 106 on opposite outer edges of cushions 40 and 42, respectively. With the head restraining device 20 thus assembled, the head of the victim 50 is essentially secured relative to the bottom portion 12 of the rescue and transportation device 10 to thereby immobilize the head and prevent lateral or forward movement of the head of the victim 50. With the head and feet of the victim thus securely restrained, the left side flap 26 is placed in overlapping position relative to the body of victim 50 with the right side flap 24 then pivoted in tight abutting relation until the Velcro fasteners 28 on the undersurface thereof lockingly engage mating aligned Velcro fasteners 29 on the outer surface of side flap 26. As can be seen in FIG. 7, the mating Velcro strips 28 and 29 are positioned in a lateral direction to permit adjustment in the lateral direction to accommodate the bodies of victims of various weights and dimensions.

At this point, with the side flaps 24 and 26 suitably fastened, referring again also to FIGS. 1, 2 and 4, the vertical or longitudinal webbing including webs 54 and 56 have the portion thereof not sewn to the bottom portion 12 brought about lengthwise over the front of the victim until the loops 58 and 60 are in aligned relation. At this juncture, the free ends of lateral webs 66, 68 and 70 are suitably locked or fastened to the D-rings 67, 69 and 71, respectively, of the lateral webs 66', 68' and 70', respectively, which are secured to the undersurface of the bottom portion 12 of the flexible outer covering of the device 10. With the lateral webs pulled taut, the body of the victim 50 along with the head is substantially immobilized within the device 10. If a manual transportation effort is effected at this point, it can be accomplished in one manner by persons gripping the flexible strap handles 76, 78, 80 and 82 for moving the victim 50. If the poles 72 and 74 are not utilized, the body's own weight and physical characteristics when confined and immobilized as hereinabove described, produce a sufficiently rigid unit with minimum flexing of the body to permit movement of the victim from confined spaces. With the cross webs 66, 68 and 70 located adjacent the knees, hips and chest of the victim, each of these portions of the body is restrained to preclude sliding of the body within the device 10, thereby distributing the weight of the body. Even in the vertical position shown in FIG. 2, with the victim suspended, the vertical or longitudinal webs 54 and 56 are in a state of tension with only 20 to 25 percent of the weight of the body being exerted on the reinforcing members of the foot end 22 of the device 10. A similar percentage of the weight is distributed on each of the lateral webs 66, 68 and 70 to thereby preclude the full weight of the body from being exerted at one point or on one surface. Even in the horizontal position, with the flexing portions of the body being suitably "locked" by means of the lateral webs dynamically cooperating with the longitudinal web means only a slight flexing of the body occurs during transportion, thus minimizing the possibilities of complications to any injuries to the victim which may exist. By substantially surrounding the body, body heat is retained and protection of the body in the case of shock or trauma is optimized. In the event the victim is suffering from burns, an accessory pack 112 (see FIGS. 1 and 4) may be provided, the accessory pack optionally including a sterile moistened sheet in a hermetically sealed envelope. Other accessory packs may optionally be provided with disposable towels or the like for treating or administering first aid to the victim.

For life sign detection or drug administration, the side flaps 24 and 26 are provided with access openings (See FIG. 7) such as access opening 32 which includes a flap having suitable fastening means such as Velcro strips 114 and 116, respectively, in mating alignment to permit access opening 32 to be opened, if necessary, or closed to maintain protection for the victim. These access openings as shown in FIG. 2 are positioned to be accessible to the arms and legs of the victim.

With reference again to FIG. 2, the poles 72 and 74 may optionally be employed by insertion into longitudinally extending slots adjacent the outer edges of the bottom portion 12 of the outer covering to permit the victim to be carried much as in the manner of a conventional stretcher unit. If the device 10 has to be lifted vertically by means of a hook device 62, the spreader bar 64 is affixed to the longitudinal webs 54 and 56 about the head restraining device 20 to keep the webs 54 and 56 from the face of the victim while precluding turning of the victim 50 during the vertical assent. The spreader bar 64 is a flexibly cloth covering containing a rigid bar member therein, with fastening means such as Velcro strips on one surface thereof for permitting the spreader bar 64 to be readily assembled and disassembled as well as to permit sliding thereof to the desired position.

The rescue and transportation device 10 according to the invention provides means for restraining the feet and head of the victim with means for substantially surrounding the victim by a flexible outer covering with lateral support means for inhibiting movement of the flexing portions of the body with longitudinal web means interconnected with the lateral support means to substantially immobilize the body and distribute the weight of the body over the bottom portion 12 of the flexible outer covering. In the preferred embodiment, man-made materials are utilized to prevent deterioration or contamination of the unit and to permit dry cleaning. Readily releasable fastening means are employed to permit adjustment to accommodate the various sizes and weights of victims and disposable accessories such as the sheet liner or the like are employed to permit the unit to be readily reused. By the utilization of the rescue and transportation device according to the invention, the amount of space occupied by each victim in a rescue vehicle, be it a land vehicle or helicopter, is generally the space occupied by the body itself, thereby enabling a given rescue vehicle to accommodate more victims. With conventional stretchers or rescue baskets, the amount of space utilized in a rescue vehicle is dictated by the overall configuration of the generally rigid stretcher or basket structure. Furthermore, the rescue and transportation device according to the invention permits removal of the victim in a substantially immobile position while minimizing the possibility of complications of existing injuries.

While there has been shown and described a preferred embodiment, it is to be understood that various other adaptations and modifications may be made within the spirit and scope of the invention.

We claim:

1. In a device for the rescue and transportation of a victim, said device comprising:
    a flexible outer covering having a central bottom portion for receiving the victim, said bottom portion having a head end and a foot end with longitudinally extending first and second side flaps configured for overlapping relation to generally surround the body of the victim;
    foot supporting means on said foot end for restraining the feet of the victim, said foot supporting means including a foot flap having means for securing the free end thereof to said bottom portion;
    laterally extending pocket means in said foot flap for receiving generally rigid slat means therein;
    head restraining means releasably coupled to said head end for generally fixedly positioning the head of the victim relative to said head end;
    a first webbing member formed in a continuous loop having an overall length at least twice the length of said bottom portion, said first webbing member being at least partially secured to the undersurface of said bottom portion, said webbing member being configured for lengthwise encircling of the flexible outer covering with the body therein with the loop ends in generally aligned relation;
    first, second and third lateral webbing members at least partially secured to said continuous loop webbing member, said first, second and third lateral webbing members being positioned for laterally encircling said flexible outer covering adjacent the knees, waist and chest area of the victim therein; and
    laterally disposed pocket means within said head end for receiving at least one reinforcing slat member, said device substantially immobilizing the body of the victim therein.

2. The combination according to claim 1 wherein said flexible outer covering has flexible handle means secured to the bottom portion thereof for transporting the victim.

3. The combination according to claim 2 wherein said flexible outer covering has longitudinally extending slots formed on opposite sides of the exterior of said bottom portion for receiving poles therein for transporting the victim.

4. The combination according to claim 3 wherein said head restraining means includes cushion means contoured for receiving the head of the victim therein and fastening means for fastening said cushion means to said head end.

5. The combination according to claim 4 wherein said cushion means includes a pair of contoured cushion members in a flexible outer covering hingedly coupling said cushion members together for lateral adjustment.

6. The combination according to claim 5 wherein said head restraining means further includes a flexible strap member having means for securing the free ends thereof to the outer covering of said cushion members, said strap member being configured for positioning across a portion of the head of the victim whereby to prevent movement of the head of the victim away from said head end.

7. The combination according to claim 6 wherein said device further includes spreader means for securing to said first webbing member adjacent said head end of said bottom portion for spacing the loop end of said first webbing member in proximity to the face of the victim.

8. In a device for the rescue and transportation of a victim, said device comprising:
a flexible outer covering having a central bottom portion for receiving the victim, said bottom portion having a head end and a foot end with longitudinally extending first and second side flaps configured for overlapping relation to generally surround the body of the victim;
a foot supporting flap on said foot end for restraining the feet of the victim;
cushion means releasably coupled to said head end for generally restraining the head of the victim relative to said head end;
lateral reinforcing means in said bottom portion and said foot supporting flap for providing rigidity adjacent said head end and said foot end; and
webbing means for encircling said flexible outer covering lengthwise and laterally relative to the body of the victim therein, said foot supporting flap, said cushion means and said webbing means substantially immobilizing the body of the victim.

9. The combination according to claim 8 wherein said cushion means includes a pair of contoured cushion members in a flexible outer covering hingedly coupling said cushion members together for lateral adjustment to accommodate varying head sizes.

10. The combination according to claim 9 wherein said cushion means further includes a flexible strap member having means for securing the free ends thereof to said cushion members, said strap member being configured for positioning across a portion of the head of the victim whereby to prevent movement of the head of the victim away from said head end.

* * * * *